(12) United States Patent
Tkaczyk et al.

(10) Patent No.: US 8,659,148 B2
(45) Date of Patent: Feb. 25, 2014

(54) TILEABLE SENSOR ARRAY

(75) Inventors: John Eric Tkaczyk, Delanson, NY (US); Lowell Scott Smith, Niskayuna, NY (US); Charles Edward Baumgartner, Niskayuna, NY (US); Robert Gideon Wodnicki, Niskayuna, NY (US); Rayette Ann Fisher, Niskayuna, NY (US); Charles Gerard Woychik, Niskayuna, NY (US); Robert Stephen Lewandowski, Amsterdam, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/956,194

(22) Filed: Nov. 30, 2010

(65) Prior Publication Data

US 2012/0133001 A1     May 31, 2012

(51) Int. Cl.
*H01L 23/34* (2006.01)
(52) U.S. Cl.
USPC .......................... 257/724; 257/722; 257/723
(58) Field of Classification Search
USPC ................................................ 257/722–724
IPC ..................................................... H01L 51/42
See application file for complete search history.

(56) References Cited

U.S. PATENT DOCUMENTS

| | | | |
|---|---|---|---|
| 5,099,128 A * | 3/1992 | Stettner | 250/370.11 |
| 7,282,382 B2 | 10/2007 | Rieve et al. | |
| 7,289,336 B2 | 10/2007 | Burdick, Jr. et al. | |
| 7,423,335 B2 | 9/2008 | Yang et al. | |
| 2008/0068815 A1 | 3/2008 | Astley et al. | |
| 2008/0157250 A1* | 7/2008 | Yang et al. | 257/433 |
| 2008/0165921 A1 | 7/2008 | Tkaczyk et al. | |

FOREIGN PATENT DOCUMENTS

| WO | 2005047859 A2 | 5/2005 |
|---|---|---|
| WO | 2008038183 A1 | 4/2008 |

* cited by examiner

Primary Examiner — Eva Yan Montalvo
(74) Attorney, Agent, or Firm — Scott J. Asmus

(57) ABSTRACT

A method for forming a tileable detector array is presented. The method includes forming a detector module, where forming the detector module includes providing a sensor array having a first side and a second side, where the sensor array includes a first plurality of contact pads disposed on the second side of the sensor array, disposing the sensor array on an interconnect layer, where the interconnect layer includes a redistribution layer having a first side and a second side, where the redistribution layer includes a second plurality of contact pads disposed on the first side, an integrated circuit having a plurality of through vias disposed therethrough, where a first side of the integrated circuit is operationally coupled to the second side of the redistribution layer, where the sensor array is disposed on the interconnect layer such that the first plurality of contact pads on the second side of the sensor array are aligned with the second plurality of contact pads on the first side of the redistribution layer, operationally coupling the first plurality of contact pads on the second side of the sensor array to the second plurality of contact pads on the redistribution layer to form a sensor stack, coupling the sensor stack to a substrate to form the detector module, and tiling a plurality of detector modules on a second substrate to form the tileable detector array.

19 Claims, 10 Drawing Sheets

TILEABLE SENSOR ARRAY

BACKGROUND

Embodiments of the present disclosure relate to sensor arrays, and more particularly to construction of modular sensor arrays.

Sensors or transducers are devices that transform input signals of one form into output signals of a different form. Commonly used transducers include light sensors, heat sensors, and acoustic sensors. An example of an acoustic sensor is an ultrasonic transducer. In ultrasound devices, the transducers transform signals of electrical energy into acoustic energy or produce electrical signals from absorbed sound waves.

Various applications, such as biomedical non-invasive diagnostics and non-destructive testing (NDT) of materials entail the use of sensor arrays, where the sensors are often configured in two-dimensions (that is, the X-Y plane). For example, ultrasonic transducer arrays are used in medical imaging, non-destructive evaluation (NDE) and other applications.

Applications such as medical and industrial imaging, non-destructive testing (NDT), security, baggage scanning, astrophysics and medicine may entail the use of sensors that encompass large areas. It may be noted that in the context of X-ray scanners and a single photon emission computed tomography (SPECT) imaging system, the large area sensor may include a sensor having an area of about 20 cm×20 cm for cardiac imaging and a sensor having an area of about 42 cm×42 cm for chest radiography. Also, for a computed tomography (CT) imaging system, the large area sensors may include sensors having an area of about 16 cm×90 cm. In the field of medical diagnostics, such as, but not limited to, X-ray, CT, ultrasound and mammography, it may be desirable to employ sensors that encompass large areas. For instance, in an X-ray imaging system, large area transducers may be necessary to encompass the area of the X-ray detector. Also, screening for internal bleeding and tumors entails use of much larger sensor arrays, typically on the order of 300 $cm^2$. Moreover, in non-medical applications even larger arrays may be desired.

Currently available techniques typically form such large arrays by arranging a large number of transducer modules in rows and columns on one side of a connecting means, such as an interposer, and a corresponding number of integrated circuits on the other side of the connecting means. Unfortunately, this entails an increased wire density of the interposer to handle the circuit load, especially as the pitch on both the sensors and the integrated circuits decreases. Performance of such large area transducers is significantly degraded when there are significant variations in spacing between modules.

Moreover, various large area applications entail use of large area sensors of different sizes and shapes. The complexities and costs associated with building a single transducer to encompass a large area can be very significant. Furthermore, there are limitations of the manufacturing technologies with regard to the maximum size of the large area sensors that can be profitably manufactured. Additionally, the expenses incurred while repairing the large area sensors may be considerable.

It would therefore be desirable to develop a sensor module design that allows assembly of large area sensor arrays in order to circumvent associated problems, such as complexities and costs associated with manufacturing and repairing a single large area sensor. Furthermore, it would be desirable to tile the sensor modules efficiently to form a high-density large area sensor array in order to minimize system size, complexity, interconnect lengths and enhance the performance of the sensor arrays.

BRIEF DESCRIPTION

In accordance with aspects of the present technique, a method for forming a tileable detector array is presented. The method includes forming a detector module, where forming the detector module includes providing a sensor array having a first side and a second side, where the sensor array includes a first plurality of contact pads disposed on the second side of the sensor array, disposing the sensor array on an interconnect layer, where the interconnect layer includes a redistribution layer having a first side and a second side, where the redistribution layer includes a second plurality of contact pads disposed on the first side of the redistribution layer, an integrated circuit having a plurality of through vias disposed therethrough, where a first side of the integrated circuit is operationally coupled to the second side of the redistribution layer, where the sensor array is disposed on the interconnect layer such that the first plurality of contact pads on the second side of the sensor array is aligned with the second plurality of contact pads on the first side of the redistribution layer, operationally coupling the first plurality of contact pads on the second side of the sensor array to the second plurality of contact pads on the first side of the redistribution layer to form a sensor stack, coupling the sensor stack to a first substrate to form the detector module, and tiling a plurality of detector modules on a second substrate to form the tileable detector array.

In accordance with another aspect of the present technique, a tileable detector array is presented. The tileable detector array includes a first substrate having a first side and a second side, a plurality of detector modules arranged on the first side of the first substrate, where each of the plurality of detector modules includes a sensor array having a first side and a second side, where a first plurality of contact pads is disposed on the second side of the sensor array, an interconnect layer including a redistribution layer having a first side and a second side, where the redistribution layer includes a second plurality of contact pads disposed on the first side of the redistribution layer, an integrated circuit having a plurality of through vias disposed therethrough, where a first side of the integrated circuit is operationally coupled to the second side of the redistribution layer, where the sensor array is disposed on the interconnect layer such that the first plurality of contact pads on the second side of the sensor array is aligned with the second plurality of contact pads on the first side of the redistribution layer, and where the first plurality of contact pads on the second side of the sensor array is operationally coupled to the second plurality of contact pads on the redistribution layer, and coupling means disposed on the second side of the integrated circuit, where the plurality of detector modules is coupled to the first side of the first substrate via the coupling means disposed on the second side of the integrated circuit.

In accordance with yet another aspect of the present technique, a method for forming a detector module is presented. The method includes providing a sensor array having a first side and a second side, where the sensor array includes a first plurality of contact pads disposed on the second side of the sensor array, providing an interposer having a first side and a second side, where the interposer includes a first set of contact pads disposed on the first side of the interposer and a second set of contact pads on the second side of the interposer, affixing a first support structure to the second side of the interposer, coupling the sensor array to the first side of the interposer by affixing the first plurality of contact pads disposed on the second side of the sensor array to the first set of contact pads disposed on the first side of the interposer to form a sensor array interposer stack, affixing a second support structure to the first side of the interposer, sawing off the first support structure, attaching the sensor array interposer stack to an interconnect layer to form a sensor stack, and coupling the sensor stack to a substrate to form the detector module.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, methods for forming detector modules and various embodiments of detector modules are presented. By employing the methods of forming the detector modules and detector modules described hereinafter, a two-dimensional (2D) high-density tileable large area detector array may be formed.

Although, the exemplary embodiments illustrated hereinafter are described in the context of a detector module configured for use in a medical imaging system such as an ultrasound imaging system, it will be appreciated that use of the detector module in other imaging systems, such as, but not limited to an X-ray imaging system, a computed tomography (CT) imaging system, a magnetic resonance (MR) imaging system, a positron emission tomography (PET) imaging system, a SPECT imaging system, a photo-acoustic tomography imaging system, and the like are also contemplated in conjunction with the present technique. Furthermore, use of the detector module in other applications such as equipment diagnostics and inspections, baggage inspections, security applications is also envisaged.

Figure 1:
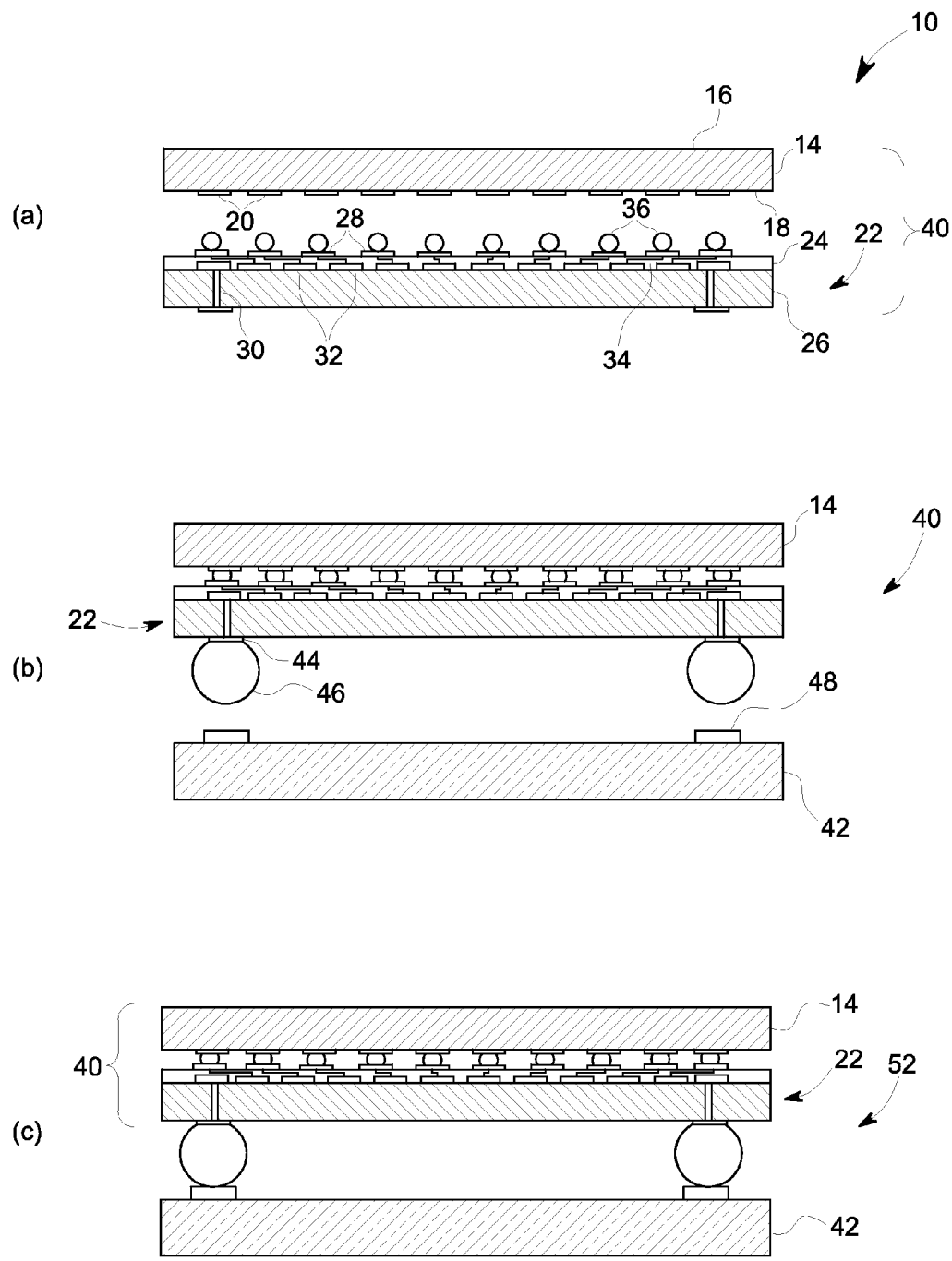
FIG. 1 is a diagrammatic illustration of a method of forming a sensor module, in accordance with aspects of the present technique.

Turning now to the drawings, and referring to FIG. 1, a diagrammatical illustration 10 of a method of forming a sensor module for use in a system, such as, but not limited to an ultrasound scanner, an X-ray detector, or a CT imaging system, is illustrated. The sensor module so formed may be used to sense a plurality of input signals. As used herein, the term "sensor module" is used to refer to a stack of a sensor array that is coupled to an interconnect layer. Furthermore, as used herein, the term "sensor array" is used to refer to an arrangement of one or more sensors or sensor elements.

As illustrated in FIG. 1, the method includes providing a sensor array 14, as depicted by FIG. 1(a). This sensor array 14 may include a plurality of sensors (not shown). Sensors are devices that are generally used to convert at least one of a sound, a temperature, a pressure, a light or other signals to or from an electronic signal. In the exemplary embodiment illustrated in FIG. 1, the sensor array 14 includes a plurality of individual sensors (not shown) configured to sense a plurality of input signals. For example, the sensors that make up the sensor array 14 may include a plurality of sensor devices, such as, but not limited to, a photodiode, a back-illuminated photodiode, an acoustic sensor, a temperature sensor, or an electromagnetic radiation sensor. Additionally, the sensors may also include micro-electromechanical systems (MEMs) devices, such as, but not limited to, capacitive micro-machined ultrasonic transducers (cMUTs).

Furthermore, the sensor array 14 has a first side 16 and a second side 18. In one embodiment, the first side 16 of the sensor array 14 is configured to receive the input signals. By way of example, in an ultrasound imaging system, the first side 16 of the sensor array 14 is configured to receive incident acoustic signals. Also, a first plurality of contact pads 20 is disposed on the second side 18 of the sensor array 18. These contact pads 20 are configured to facilitate coupling the sensor array 14 to other electronics. It may also be noted that the length of the sensor array 14 may be in a range from about 3 mm to about 12 cm. Also, the sensor array 14 may have a thickness in a range from about 50 µm to about 1 mm.

Furthermore, at step 12, the sensor array 14 is disposed adjacent to an interconnect layer 22. In accordance with aspects of the present technique, the interconnect layer 22 includes a redistribution layer 24 and an integrated circuit 26 operationally coupled to one another. The redistribution layer 24 is configured to match an interface of the sensor array 14 to an interface of the integrated circuit 26. Particularly, the redistribution layer 24 provides a fan out of a cell array on the integrated circuit 26 to mate with the array of sensors in the sensor array 14.

Moreover, the redistribution layer 24 has a first side and a second side. Additionally, the redistribution layer 24 includes a second plurality of contact pads 28 disposed on the first side of the redistribution layer 24. In particular, the second plurality of contact pads 28 is arranged on the first side of the redistribution layer 24 such that the arrangement of the second plurality of contact pads 28 matches the arrangement of the first plurality of contact pads 20 disposed on the second side of the sensor array 14. These contact pads 28 are configured to provide an input to the integrated circuit 26. By way of example, the second plurality of contact pads 28 is configured to facilitate communicating an output of the sensor array 14 as an input to the integrated circuit 26 for processing. It may be noted that the redistribution layer 24 may be formed using a thin film technique or a thick film technique. The redistribution layer 24 that is fabricated using the thin film technique may have a thickness in a range from about 0.1 μm to about 2.0 μm. Alternatively, the redistribution layer 24 that is fabricated using the thick film technique may have a thickness in a range from about 2.0 μm to about 25 μm. Also, the length of the redistribution layer 24 may be in a range from about 10 mm to about 50 mm on a side to match the width of the sensor and application specific integrated circuit (ASIC) components.

In certain embodiments, the integrated circuit 26 may include an application specific integrated circuit (ASIC). The ASIC 26 may include processing circuitry (not shown) that facilitates the functionality of the ASIC. Additionally, in accordance with aspects of the present technique, the integrated circuit 26 includes one or more through vias 30 disposed therethrough. Further, in one embodiment, the through vias 30 may include through silicon vias (TSVs). As will be appreciated, a through silicon via is a vertical connection that passes completely through a silicon wafer or die and is configured to aid in coupling devices in a package while reducing the footprint of the package. In the present embodiment, the TSVs 30 in the integrated circuit 26 allow for power signals, ground signals, analog signals and/or digital signals to be routed directly from the sensor array 14 through the TSVs 30 directly under the die. Moreover, in certain embodiments, the number of TSVs 30 in the integrated circuit 26 may be in a range from about 32 to 512. Furthermore, a third plurality of contact pads 32 is disposed on the first side of the integrated circuit 26. These contact pads 32 are inputs to the integrated circuit 26. In certain embodiments, the contact pads 32 may include metal pads.

As previously noted, the second plurality of contact pads 28 facilitates a distribution of connections between the first plurality of contact pads 20 and the third plurality of contact pads 32. By way of example, the first plurality of contact pads 20 may be arranged in an (32×32) electrode array and having a pitch of about 0.150 mm. Similarly, the third plurality of contact pads 32 may be arranged in a determined pattern, such as an (32×32) ASIC cell array and having a pitch of about 0.125 mm. Accordingly, the second plurality of contact pads 28 is configured to provide an interface to match the pattern of the first plurality of contact pads 20 with the pattern of the third plurality of contact pads 32. Additionally, metal lines 34 operationally couple the second plurality of contact pads 28 to the third plurality of contact pads 32. Particularly, these metal lines 34 are configured to transfer voltages and/or currents between the sensor array 14 and the processing circuits in the integrated circuit 26.

With continuing reference to step 12, the sensor array 14 is disposed adjacent to the interconnect layer 22 such that the first plurality of contact pads 20 on the second side 18 of the sensor array 14 is aligned with the second plurality of contact pads 28 on the first side of the redistribution layer 24. Subsequently, the sensor array 14 is operationally coupled to the interconnect layer 22 to form a sensor stack 40. In accordance with aspects of the present technique, the sensor array 14 is operationally coupled to the interconnect layer 22 using a high temperature attach process. As used herein, the term "high temperature attach process" is used to refer to a bonding process that effects a bond between the sensor array 14 and the interconnect layer 22 while operating in temperature range from about 160° C. to about 230° C. Accordingly, a solder alloy having a high melting temperature is used. Use of this solder alloy ensures that this interconnect of the sensor array does not reflow during a subsequent solder assembly process. By way of example, a conventional Sn—3.0Ag—0.5Cu (305SAC) alloy which melts at about 217° C. is used for this coupling. Alternatively, the high temperature attach process may incorporate use of an anisotropically conductive adhesive formulated as conductive particles dispersed in a high temperature adhesive such as an epoxy wherein conduction is attained only in one direction.

Furthermore, in one embodiment, a high temperature solder flip chip attach process is used to operationally coupled the sensor array 14 to the interconnect layer 22. As will be appreciated, a flip chip attach process facilitates a direct electrical connection of face-down electronic components onto substrates, circuit boards, or other carriers by means of conductive bumps on chip bond pads. To that end, attaching means 36 configured to facilitate operationally coupling the sensor array 14 to the interconnect layer 22 is disposed on each of the first plurality of contact pads 20 and/or each of the second plurality of contact pads 28. In one embodiment, the attaching means 36 may include conductive bumps, where the conductive bumps include solder bumps formed using a metal alloy having a relatively high melting point. For example, the solder bumps may be formed using a high melt lead (Pb)-rich solder alloy having a melting point in a range from about 250° C. to about 320° C. In certain other embodiments, a Pb-rich solder bump, having a composition of 97Pb-3Sn that melts at about 320° C. may be used. To that end, a standard plating process is used to deposit the alloy on the second plurality of contact pads 28, for example and then reflowed to produce the Pb-rich bumped configuration. The Pb-rich bumped interconnect layer 22 is then placed in contact with the contact pads 20 on the sensor array 14 and reflowed. Alternatively, lead free solder bumps like SnAgCu or Ag—Sn alloys may be used. Moreover, in certain other embodiments, the conductive bumps 36 may be disposed on the contact pads 20 or the contact pads 28 by evaporation, stencil printing, injection molding, electroplating, screen printing, solder paste or needle depositing.

By way of example, in one embodiment, the solder bumps 36 may be deposited on the contact pads 28 to form a bumped interconnect layer. Subsequently, the bumped interconnect layer is operationally coupled to the sensor layer 14 by attaching the contact pads 20 to the contact pads 28 using the solder bumps 36 and heating the assembly to effect the bonding by a solder connection. This assembly may be referred to as a sensor stack 40.

Furthermore, the attaching means 36 may also include a plated bump, a gold stud bump or an adhesive bump based on the application. It may also be noted in certain other embodiments, the attaching means 36 may include copper pillars. In yet another embodiment, a transient liquid phase (TLP) bonding process may be used to operationally couple the sensor array 14 to the interconnect layer 22.

Once the sensor stack 40 is formed, in accordance with further aspects of the present technique, the sensor stack 40 is operationally coupled to a substrate 42 to form a sensor module, as depicted by FIG. 1(*b*). The substrate 42 is formed using a rigid and stable material such as a ceramic or an organic material such as Teflon (polytetrafluoroethylene (PTFE)). In one embodiment, the substrate 42 includes a low-coefficient of thermal expansion (CTE) engineered interposer produced by Endicott Interconnect Inc., Endicott, N.Y. that has a copper-invar-copper metal core with a Rogers 2800 Teflon build-up laminate on both sides. A 11-layered substrate is produced that has a nominal CTE of 11 ppm/° C. and has been shown to produce very reliable, flip chip and BGA solder interconnects when assembled to a standard FR4 board. This substrate has been given the trademark name of HyperBGA by Endicott Interconnect. To couple the sensor stack 40 to the substrate 42, one or more metal pads 44 are disposed on the second side of the interconnect layer 22. Subsequently, a solder bump 46 or other attaching means is disposed on each of the one or more metal pads 44. Furthermore, a set of metal pads 48 is disposed on the substrate 42. The solder bumps 48 aid in coupling the sensor stack 40 to the substrate 42. Particularly, these metal pads 48 are arranged on the substrate 42 such that the pattern of the metal pads 48 matches the pattern of the metal pads 44 on the interconnect layer 22. Once the solder bumps 48 are formed, in accordance with aspects of the present technique, the sensor stack 40 is coupled to the substrate 42 employing a low temperature attach process to form the sensor module 52, as depicted by FIG. 1(*c*). In one embodiment, a flip chip solder process may be used to attach the sensor stack 40 to the substrate 42 while operating in a temperature range from about 130° C. to about 200° C. Particularly, a Pb alloy having a melting temperature that is lower than the melting temperature of the alloy used to couple the sensor array 14 to the interconnect layer 22 is used to couple the sensor stack 40 to the substrate 42. By way of example, a lower melt eutectic Sn—Bi alloy that melts at about 138° C. is used for coupling the solder bumps 46 on the interconnect layer 22 to the substrate 42.

Also, coupling the sensor array 14 to the interconnect layer 22 employing a high temperature attach process and using attaching means 36 having a higher melting point than the melting point of the attaching means 46 used to couple the sensor stack 40 to the substrate 42 advantageously prevents secondary reflow when the sensor stack 40 is attached to the substrate 42.

Figure 2:
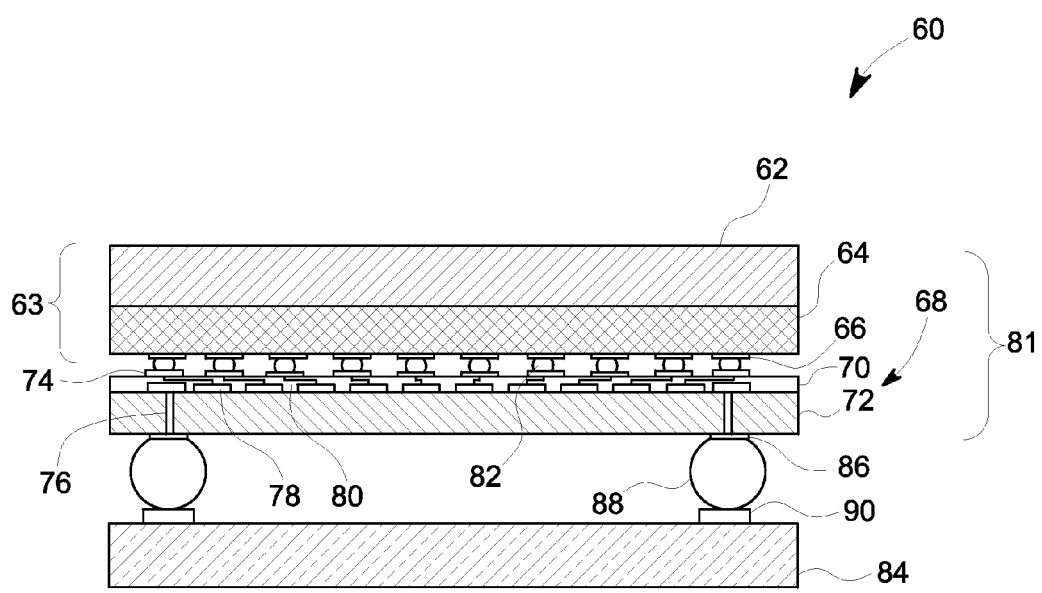
FIG. 2 is a diagrammatic illustration of another embodiment of a sensor module, in accordance with aspects of the present technique.

In the embodiment of the sensor module 52 depicted in FIG. 1, the sensor array 14 is directly attached to the interconnect layer 22. In accordance with further aspects of the present technique, the sensor array 14 may instead be indirectly attached to the interconnect layer 22. To that end, an interposer may be employed to facilitate the indirect coupling. Turning now to FIG. 2, another embodiment 60 of a sensor module is depicted. In the embodiment illustrated in FIG. 2, a sensor array 62 is operationally coupled to an interposer 64. As will be appreciated, an interposer is an electrical interface routing between one connection to another. Particularly, the purpose of the interposer is to spread a connection to a different pitch or to reroute a connection to a different connection. It may be noted that in certain embodiments the interposer 64 may include a rigid interposer, while in certain other embodiments, the interposer 64 may include a flexible interposer. By way of example, the rigid interposer may include a FR4 material, while the flexible interposer may include a polyimide. Additionally, the interposer 64 may include a ceramic material or an organic material.

In a presently contemplated configuration, a second side of the sensor array 62 is coupled to a first side of the interposer 64 to form a sensor array interposer stack 63. Also, a first plurality of contact pads 66 is disposed on a second side of the interposer 64, where the contact pads 66 are configured to facilitate coupling the sensor array interposer stack 63 to other electronics. For example, the sensor array interposer stack 63 is coupled to an interconnect layer 68. In accordance with aspects of the present technique, the interconnect layer 68 includes a redistribution layer 70 and an integrated circuit 72 operationally coupled to one another. In the embodiment of FIG. 2, the redistribution layer 70 is configured to match an interface of the sensor array interposer stack 63 to an interface of the integrated circuit 72. In particular, the redistribution layer 70 includes a second plurality of contact pads 74 disposed on a first side of the redistribution layer 70. The second plurality of contact pads 74 is arranged on the first side of the redistribution layer 70 such that the arrangement of the second plurality of contact pads 74 matches the arrangement of the first plurality of contact pads 66 disposed on the second side of the interposer 64.

The integrated circuit 72 includes one or more through vias 76 disposed therethrough. Power signals, ground signals, analog signals and/or digital signals are routed directly from the sensor array 62 through the TSVs 76 directly under the die. Furthermore, a third plurality of contact pads 78 is disposed on a first side of the integrated circuit 72. Additionally, metal lines 80 operationally couple the second plurality of contact pads 74 to the third plurality of contact pads 78 and are configured to transfer voltages and/or currents between the sensor array 62 and the processing circuits in the integrated circuit 72.

Furthermore, the sensor array interposer stack 63 is operationally coupled to the interconnect layer 68 to form a sensor stack 81. Specifically, the sensor array interposer stack 63 is operationally coupled to the interconnect layer 68 to form a sensor stack 81 using a high temperature attach process. In one embodiment, a high temperature solder flip chip attach process is used to operationally coupled the sensor array interposer stack 63 to the interconnect layer 68. To that end, attaching means 82 configured to facilitate operationally coupling the sensor array interposer stack 63 to the interconnect layer 68 is disposed on each of the first plurality of contact pads 66 or on each of the second plurality of contact pads 74. As previously noted, the attaching means 82 may include solder balls, copper pillars, or a transient liquid phase (TLP) material.

Subsequently, the sensor stack 81 is operationally coupled to a substrate 84 to form the sensor module 60. To achieve this coupling, one or more metal pads 86 are disposed on the second side of the interconnect layer 72. Subsequently, a solder bump 88 is disposed on each of the one or more metal pads 86. Furthermore, a set of metal pads 90 is disposed on the substrate 84 to facilitate coupling the substrate 84 to the second side of interconnect layer 68. Specifically, in accordance with aspects of the present technique, the substrate 84 is coupled to the second side of interconnect layer 68 employing a low temperature attach process to form the sensor module 60.

Figure 4:
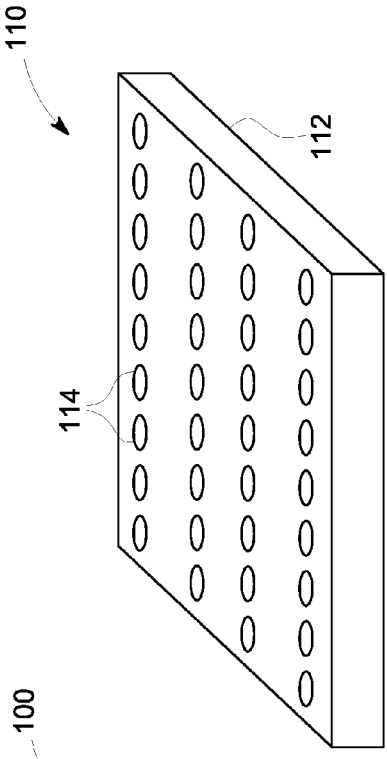
FIGS. 3-6 are diagrammatic representations of different embodiments of an integrated circuit having through silicon vias disposed therethrough and configured for use in the sensor modules of FIGS. 1 and 2.
Figure 3:
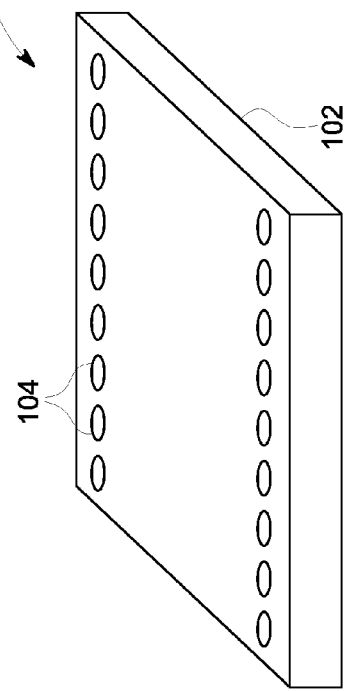
Figure 6:
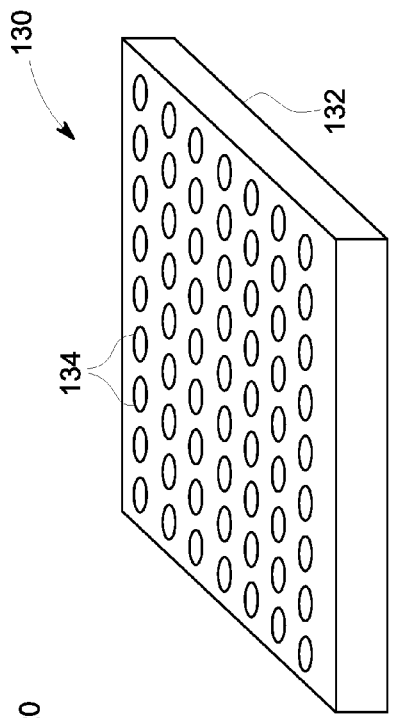
Figure 5:
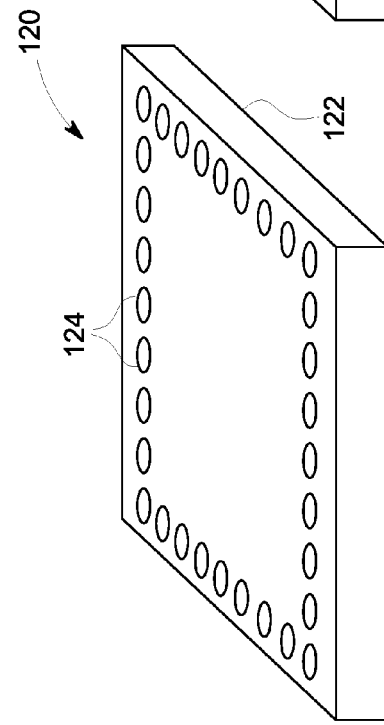

FIGS. 3-6 depict various embodiments of an integrated circuit, such as the integrated circuit 26 of FIG. 1. Particularly, in a first embodiment 100 illustrated in FIG. 3, an integrated circuit 102 having two-sided TSVs 104 disposed therethrough is depicted. The plurality of through vias 104, such as the through silicon vias (TSVs) 30 of FIG. 1, are disposed on a first side and a second side of the integrated circuit 102. It may be noted an arrangement of the TSVs on the first side of the integrated circuit 102 may be different from an arrangement of the TSVs on the second side of the integrated circuit 102, in certain embodiments. However, the arrangement of TSVs on both the first side and the second side of the integrated circuit 102 may be substantially similar, in certain other embodiments. Referring now to FIG. 4, an embodiment 110 of an integrated circuit 112 having a plurality of TSVs 114 arranged in a partial array on the integrated circuit 112 is depicted. Also, an embodiment 120 depicted in FIG. 5 shows an arrangement of TSVs 124 that are disposed along a perimeter of an integrated circuit 122. As used herein, the term "partial array" is used to refer to an array of TSVs that does not tile the full area of a die with a two-dimensional (2D) array of TSVs. In addition, an embodiment 130 of an integrated circuit 132 having a plurality of TSVs 134 arranged in a full array on the integrated circuit 132 is depicted in FIG. 6. As used herein, the term "full array" is used to refer to an array of TSVs that tiles the full area of a die with a 2D array of TSVs.

As previously noted, creating a large sensor array using conventional packaging techniques is difficult. Accordingly, it is desirable to develop a design of a sensor stack that allows building a large area detector module. Tiling is an approach that offers an attractive solution to the problems associated with building a large area sensor module. An exemplary detector module, according to the present technique may be constructed by tiling smaller, individual sensor modules, such as the sensor stack 40 (see FIG. 1) to form a large area (X, Y) detector module.

According to one embodiment of the present technique, a plurality of sensor stacks 40 is fabricated. By way of example, a wafer having the plurality of sensor stacks 40 may be fabricated. The wafer is then diced to form individual sensor stacks. The individual sensor stacks are then tested and known good sensor stacks are identified that may be advantageously used to build the large area detector module.

Figure 7:
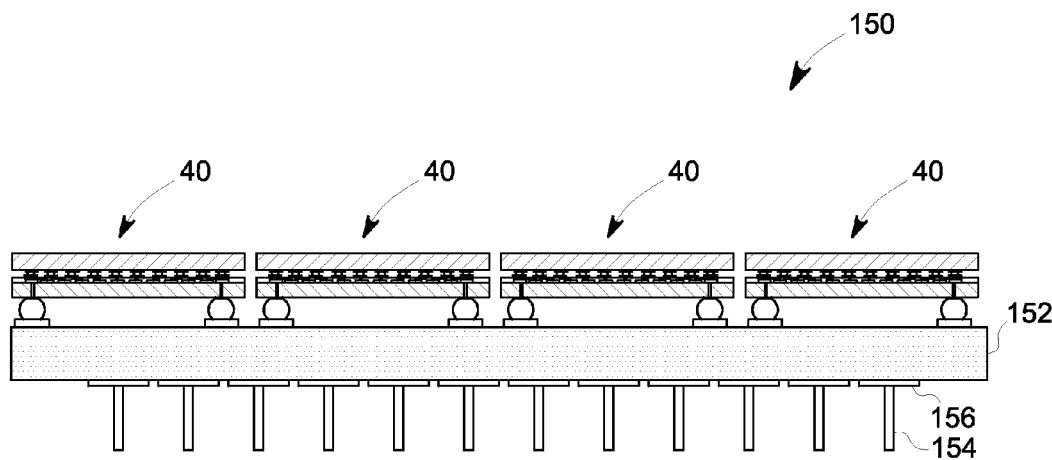
FIG. 7 is a diagrammatic illustration of one embodiment of a pluggable detector module that includes one or more sensor modules of FIG. 1 or 2, in accordance with aspects of the present technique.

Turning now to FIG. 7, one embodiment 150 of an exemplary detector module is depicted. A plurality of sensor stacks 40 (see FIG. 1) is arranged in a determined pattern on a first side of a substrate 152 to form the detector module. Typically, the substrate 152 may include a semiconductor material, such as silicon, or a flexible material, such as polyimide, although other types of materials with similar properties may be used. The substrate 152 may also include other components, such as, but not limited to, discrete electronic components.

According to aspects of the present technique, the plurality of sensor stacks 40 is attached to the substrate 152 to create a high-density tileable array of sensor stacks 40 using a flip chip solder attach process. More specifically, use of the flip chip solder attach process allows accurate placement of the sensor stacks 40 on the substrate 152 to form a very high-density detector module 150, with very tight chip-to-chip spacing. Particularly, in accordance with aspects of the present technique, the plurality of sensor stacks 40 may be disposed such that a gap between the sensor stacks 40 is substantially small. By way of example, the gap between adjacently disposed sensor stacks 40 may be in a range from about 5 µm to about 5200 µm. In some embodiments, the gap between adjacently disposed sensor stacks 40 may be in a range from about 5 µm to about 50 µm.

Furthermore, the substrate 152 may have pins disposed on a second side of the detector module 150 in order to form a pluggable detector module. Accordingly coupling means 154 are disposed on a second side of the substrate 152, where the coupling means 154 facilitate coupling the detector module 150 to other electronics. To that end, a plurality of metal pads 156 is disposed on the second side of the substrate 152. The coupling means 154 are disposed on the metal pads 156. In a presently contemplated configuration, the coupling means 154 includes one or more copper pillars. Accordingly, a copper pillar 154 is disposed on each of the metal pads 156. The combination of the plurality of sensor stacks 40 along with the substrate 152 having coupling means 154 disposed on the second side of the substrate 152 forms the pluggable detector module 150.

Figure 8:
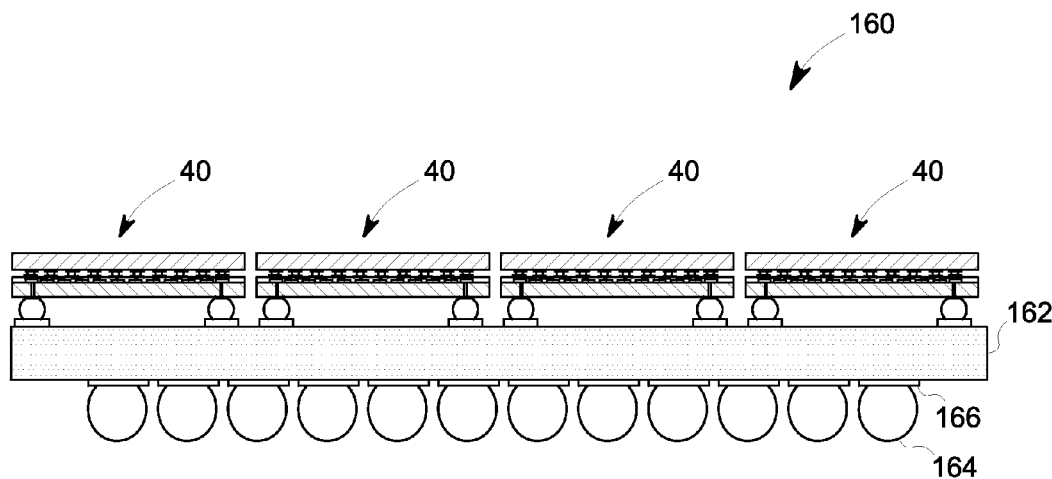
FIG. 8 is a diagrammatic illustration of another embodiment of a solderable detector module that includes one or more sensor modules of FIG. 1 or 2, in accordance with aspects of the present technique.

FIG. 8 depicts another embodiment 160 of an exemplary large area detector module. As previously noted with reference to FIG. 7, a plurality of sensor stacks 40 is arranged in a determined pattern on a first side of a substrate 162 to form the large area detector module. More specifically, multiple sensor stacks 40 are flip chip solder attached to the substrate 162 to produce a very high-density detector module 160, with very tight chip-to-chip spacing. Here again, coupling means 164 are disposed on a second side of the substrate 162, where the coupling means 164 facilitates coupling the detector module 160 to other electronics. Particularly, a plurality of metal pads 166 is disposed on the second side of the substrate 162. The coupling means 164 are disposed on the metal pads 166. Also, in the configuration of FIG. 8, the coupling means 164 includes a ball grid array (BGA). In one embodiment, the ball grid array 164 includes a plurality of solder balls that facilitates soldering the detector module 160 to a next level of package. Specifically, a solder ball 164 in the ball grid array may be disposed on each of the metal pads 166 to form the detector module 160 that is solderable to other electronics in a package.

Figure 9:
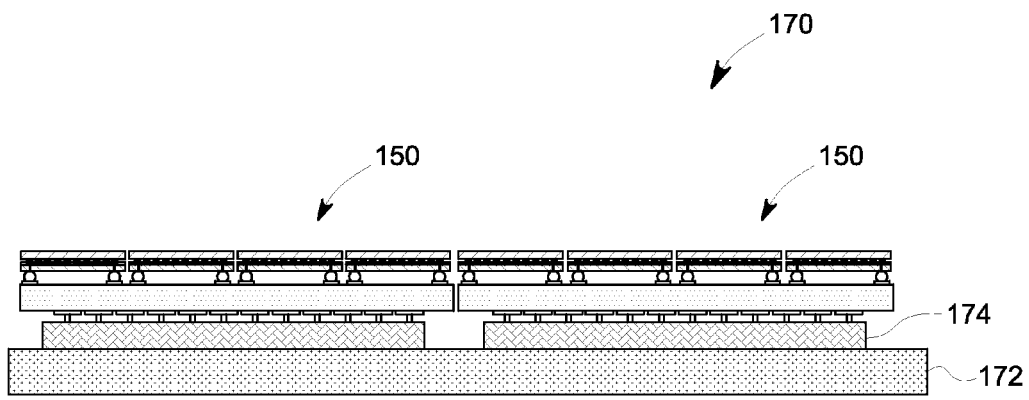
FIG. 9 is a diagrammatic illustration of one embodiment of a field replaceable unit that includes one or more pluggable detector modules of FIG. 7 or 8, in accordance with aspects of the present technique.

In accordance with further aspects of the present technique, the individual pluggable detector modules 150 of FIG. 7 may be tiled to form a larger tileable detector array. Referring now to FIG. 9, an embodiment 170 of one such large area detector array is depicted. In a presently contemplated configuration, a plurality of pluggable detector modules 150 is arranged in a determined pattern to form the larger detector array. Particularly, the individual pluggable detector modules 150 may be plugged into a motherboard 172 to create a large (M×N) tileable array, as depicted in FIG. 9. As will be appreciated, the motherboard 172 may include other components, such as, but not limited to, high voltage field programmable grid arrays (FPGAs), power conditioning circuits, regulators, direct current (DC) power supplies, and the like. Reference numeral 174 is generally representative of a socket disposed on the motherboard 172 that facilitates coupling the pluggable detector modules 150 to the motherboard 172. It may also be noted that if the detector modules 160 of FIG. 8 are used to form a large (M×N) tileable array, then the individual detector modules 160 are soldered to the motherboard 172 via the sockets 174. The design of the large area detector array 170 allows each detector module to be replaced, thereby creating a field replaceable unit (FRU) that allows for easy removal and replacement of a bad detector module.

Figure 10:
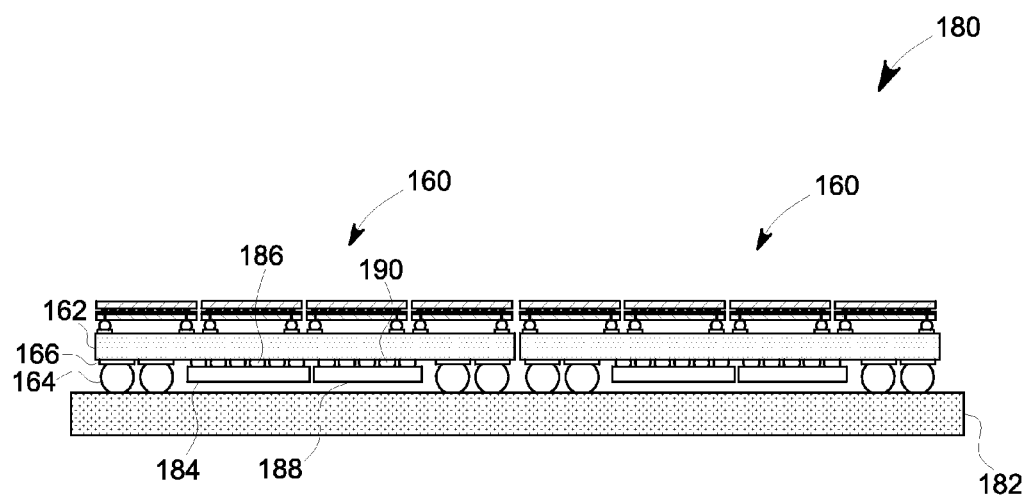
FIG. 10 is a diagrammatic illustration of one embodiment of a field replaceable unit that includes processing circuitry coupled to the one or more pluggable detector modules of FIG. 7 or 8, in accordance with aspects of the present technique.

Additionally, in accordance with further aspects of the present technique, a tiled large area array with local digital and analog signal processing may be realized. FIG. 10 depicts a cross-sectional view 180 of a tiled large area detector array. Particularly, in the embodiment illustrated in FIG. 10, a plurality of tileable detector modules, such as the detector modules 160 (see FIG. 8), is arranged in a determined pattern to form the large area detector array. Particularly, the plurality of detector modules 160 is arranged on a second substrate 182 to create a large (M×N) tileable array, as depicted in FIG. 10. The second substrate 182 may generally be referred to as a common system substrate.

As previously described with reference to FIG. 8, each tileable detector module 160 is composed of a series of tiled sensor stacks 40 arranged on the first substrate 162 (see FIG. 8). In accordance with aspects of the present technique, the detector module 160 may additionally include processing circuitry disposed on a second side of the substrate 162. The processing circuitry may include control electronics 184 and/or other front-end electronics 188. The control electronics 184 is operationally coupled to the second side of the first substrate 162 via use of solder bumps 186, in certain embodiments. Similarly, the front-end electronics 188 is also operationally coupled to the second side of the first substrate 162 via use of solder bumps 190.

The processing circuitry that includes the control electronics 184 and/or the front-end electronics 188 is used to implement local signal processing and control functions. In certain embodiments, the local signal processing and control functions include, but are not limited to, storing configuration data for the respective sensor stacks, timing and control of programming and operation of the ASICs in the respective sensor stacks, amplification, variable gain control and analog to digital converters to process the received signals from the sensor stacks, voltage regulators, supply decoupling, as well as appropriate signal conditioning and transmit/receive means for buffering the received data to a system bus for further processing. The transmit/receive means may be electronic (e.g., low-voltage differential signaling (LVDS)), optical or radio frequency (RF) in nature.

Furthermore, the second substrate 182 may include standard printed circuit board material (e.g., FR4), a silicon substrate, a ceramic substrate, flexible circuitry (e.g., capton) with a supporting rigid substrate, glass, or other materials. The second substrate 182 may be flat or may have a different shape. By way of example, the second substrate 182 may be curved, thereby aiding in forming a curved array for use in abdominal imaging. Additionally, the second substrate 182 may include appropriate signal routing for supplying power and ground as well signal transmission to and from the individual tileable modules 160. Furthermore, the second substrate 182 may also serve only as a physical support for the tileable modules 160, with interconnection between the tileable modules 160 being achieved with secondary means such as flex circuits that are attached via a connector to each tileable module 160. Moreover, the tileable modules 160 may be attached to the second substrate 182 using solder balls, stud bumps, or posts.

Figure 11:
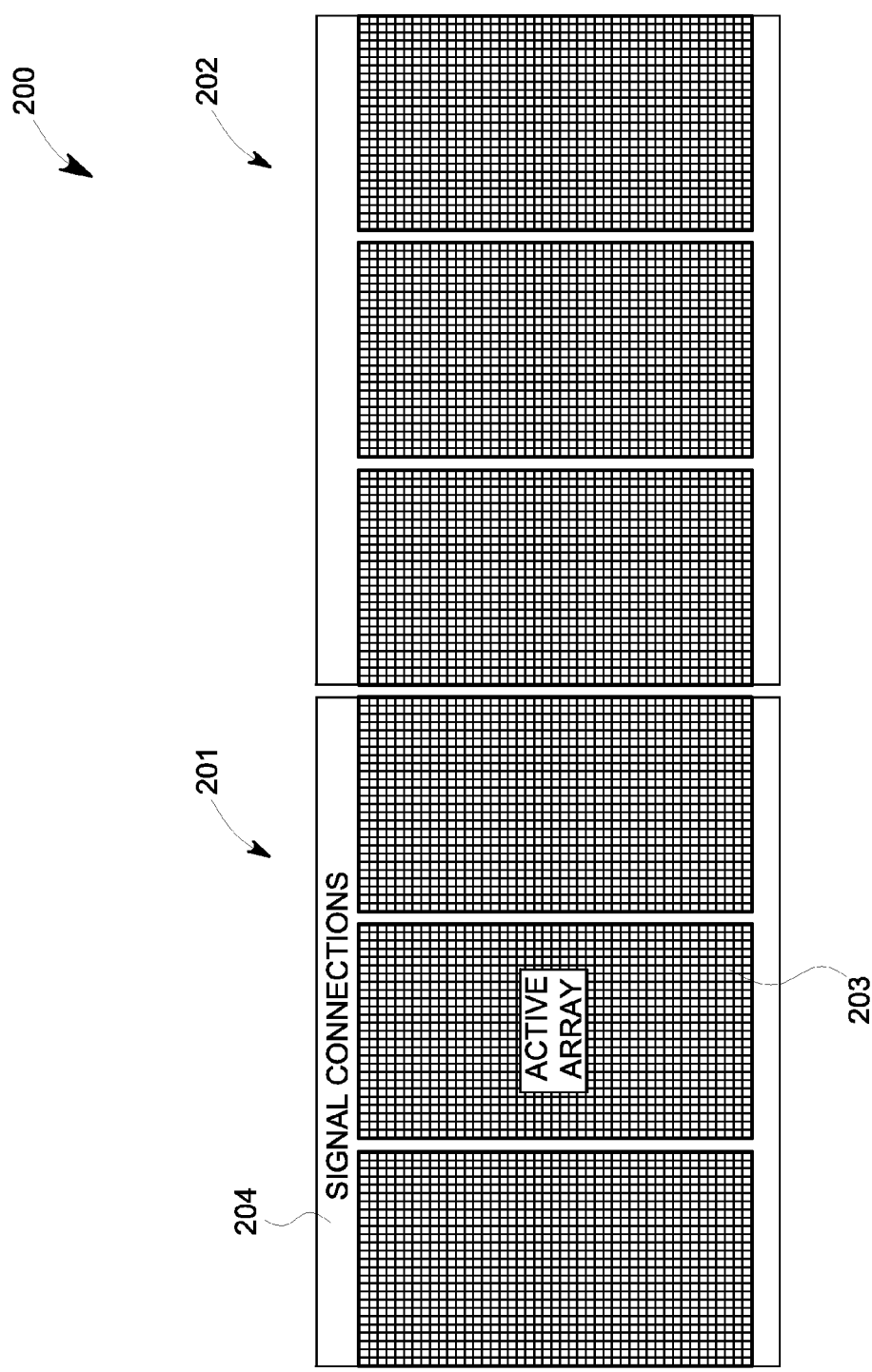
FIG. 11 is a diagrammatic illustration of a plan view of the cross-section of FIG. 10 that depicts an active array of signal connections, in accordance with aspects of the present technique.

Also, a plan view 200 of a tileable detector array is depicted in FIG. 11. Specifically, as depicted in FIG. 11, a plurality of tileable detector modules, such as the tileable detector modules 160 (see FIG. 8) may be tiled in a (2×N) configuration with minimal gaps between them. Reference numerals 201 and 202 are respectively representative of a first tileable detector module and a second detector module. In the embodiment of FIG. 11, signal connections between the tileable modules 201 and 202 may be accomplished above and below an active area of the array 203 as shown. Reference numeral 204 is generally representative of signal connections. Additionally, for a fully tiled 2D array, signal connections may be routed directly behind the array as is illustrated in the cross-sectional view of FIG. 10.

Figure 12:
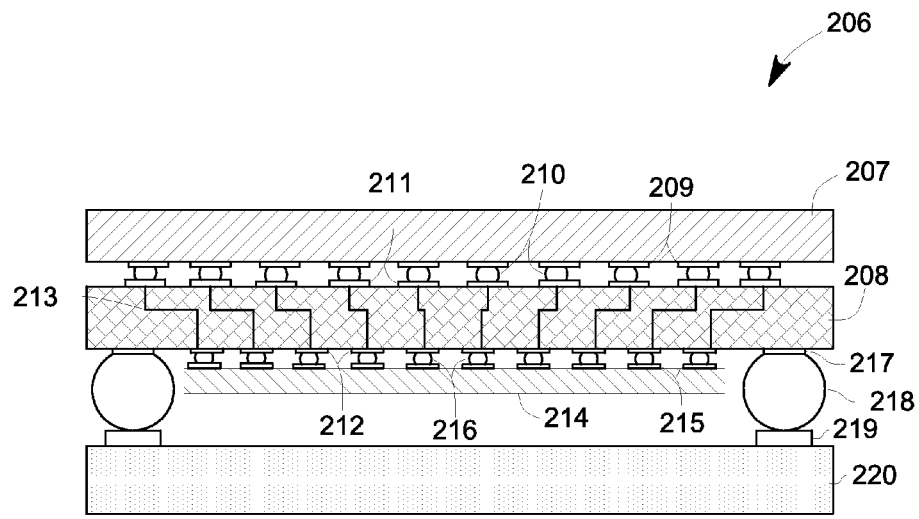
FIG. 12 is a diagrammatic illustration of yet another embodiment of a sensor module, in accordance with aspects of the present technique.

FIG. 12 is a diagrammatic illustration of another embodiment 206 of a sensor module. In the embodiment illustrated in FIG. 12, a sensor array 207 is indirectly coupled to an integrated circuit 214 via an interposer 208. Accordingly, the sensor array 207 is operationally coupled to the interposer 208. As previously noted, the interposer 208 is an electrical interface routing between one connection to another. In certain embodiments the interposer 208 may include a rigid interposer, while in certain other embodiments, the interposer 208 may include a flexible interposer. By way of example, the rigid interposer may include a FR4 material, while the flexible interposer may include a polyimide. Additionally, the interposer 208 may include a ceramic material or an organic material.

In a presently contemplated configuration, a second side of the sensor array 207 is coupled to a first side of the interposer 208 to form a sensor array interposer stack. To facilitate this coupling, a first plurality of contact pads 209 is disposed on a second side of the sensor array 207, where the contact pads 209 are configured to facilitate coupling the sensor array 207 to the interposer 208. Additionally, a second plurality of contact pads 211 is disposed on a first side of the interposer 208, while a third plurality of contact pads 212 is disposed on a second side of the interposer 208. The second plurality of contact pads 211 aids in coupling the sensor array 207 to the interposer 208. Particularly, the second plurality of contact pads 211 disposed on the first side of the interposer 208 is arranged on the first side of the interposer 208 such that the arrangement of the second plurality of contact pads 211 matches the arrangement of the first plurality of contact pads 209 disposed on the second side of the sensor array 207, in one embodiment. Additionally, metal lines 213 operationally couple the second plurality of contact pads 211 to the third plurality of contact pads 212 and are configured to transfer voltages and/or currents between the sensor array 207 and the processing circuits in an integrated circuit 214.

Moreover, in accordance with aspects of the present technique, the sensor array 207 is operationally coupled to the interposer 208 using a high temperature attach process. In one embodiment, a high temperature solder flip chip attach process is used to operationally coupled the sensor array 207 to the interposer 208. To that end, attaching means 210 configured to facilitate operationally coupling the sensor array 207 to the interposer 208 is disposed on each of the first plurality of contact pads 209 or on each of the second plurality of contact pads 211. As previously noted, the attaching means 210 may include solder balls, copper pillars, or a transient liquid phase (TLP) material.

In accordance with further aspects of the present technique, an integrated circuit 214 is operationally coupled to the second side of interposer 208. To achieve this coupling, one or more contact pads 215 are disposed on a first side of the integrated circuit 214. Specifically, in one embodiment, the one or more contact pads 215 disposed on the first side of the integrated circuit 214 is arranged on the first side of the integrated circuit 214 such that the arrangement of the one or more contact pads 215 matches the arrangement of the third plurality of contact pads 212 disposed on the second side of the interposer 208. In addition coupling means 216 is disposed on the third plurality of contact pads 212 on the second side of the interposer 208 or on the one or more contact pads 215 on the first side of the integrated circuit 214. The coupling means 216 is configured to aid in operationally coupling the integrated circuit 214 to the interposer 208. Here again, the coupling means 216 may include solder balls, copper pillars, or a transient liquid phase (TLP) material. Moreover, the integrated circuit 214 may be coupled to the interposer 208 using a high temperature attach process.

Furthermore, a set of metal pads 217 is disposed on the second side of the interposer 208. These metal pads 217 aid in coupling the stack that includes the sensor array 207, the interposer 208 and the integrated circuit 214 to a substrate 220. Particularly, the substrate 220 is coupled to the second side of the interposer 208. Additionally, metal pads 219 are disposed on a first side of the substrate 220. Coupling means 218 is disposed on the metal pads 217 or on the metal pads 219. The coupling means 218 aids in coupling the substrate 220 to the second side of the interposer 208. Specifically, in accordance with aspects of the present technique, the substrate 220 is coupled to the second side of interposer 208 employing a low temperature attach process to form the sensor module 206.

Figure 13:
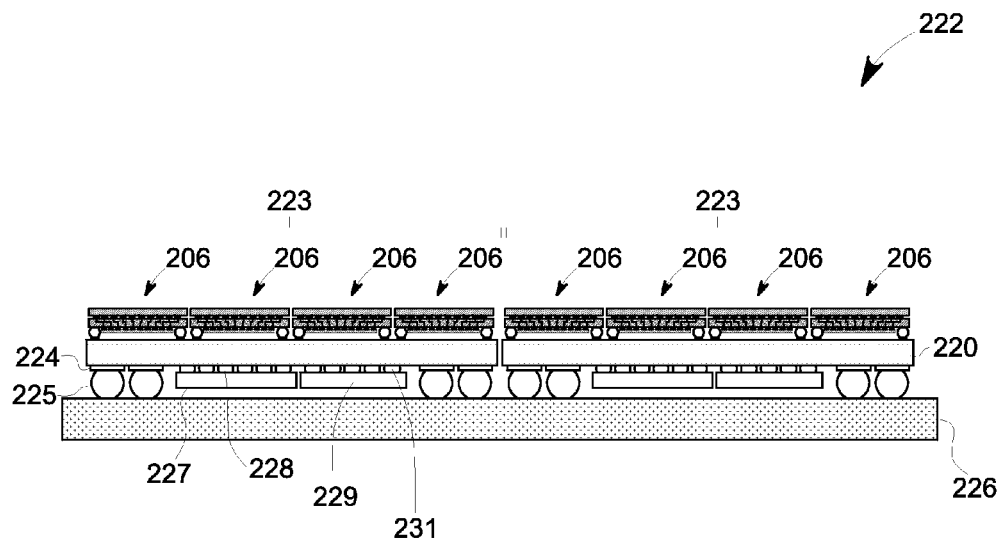
FIG. 13 is a diagrammatic illustration of one embodiment of a field replaceable unit that includes processing circuitry coupled to the one or more pluggable detector modules of FIG. 12, in accordance with aspects of the present technique.

Referring now to FIG. 13, a cross-sectional view 222 of a tiled large area detector array is depicted. Particularly, in the embodiment illustrated in FIG. 13, a plurality of tileable detector modules 223 is arranged in a determined pattern to form the large area detector array. Particularly, the plurality of detector modules 223 is arranged on a second substrate 226 to create a large (M×N) tileable array, as depicted in FIG. 13. The second substrate 226 may generally be referred to as a common system substrate.

It may be noted that each tileable detector module 223 is composed of a series of tiled sensor stacks 206 (see FIG. 12) arranged on the first substrate 220 (see FIG. 12). In accordance with aspects of the present technique, the detector module 223 may additionally include processing circuitry disposed on a second side of the substrate 220. The processing circuitry may include control electronics 227 and/or other front-end electronics 229. The control electronics 227 is operationally coupled to the second side of the first substrate 220 via use of solder bumps 228, in certain embodiments. Similarly, the front-end electronics 229 is also operationally coupled to the second side of the first substrate 220 via use of solder bumps 231.

As previously noted, the processing circuitry that includes the control electronics 227 and/or the front-end electronics 229 is used to implement local signal processing and control functions. Also, the second substrate 226 may include standard printed circuit board material (e.g., FR4), a silicon substrate, a ceramic substrate, flexible circuitry (e.g., capton) with a supporting rigid substrate, glass, or other materials. The second substrate 226 may be flat or may have a different shape. Moreover, the tileable modules 223 may be attached to the second substrate 226 using coupling means 225. The coupling means 225 may include solder balls, stud bumps, or posts. Reference numeral 224 is generally representative of metal pads disposed on the second side of the substrate 220. The coupling means 225 may be disposed on these metal pads 224 to aid in coupling the plurality of tileable detector modules 223 to the second substrate 226. In accordance with aspects of the present technique, the plurality of tileable detector modules 223 may be coupled to the second substrate 226 using a low temperature attach process.

Figure 14:
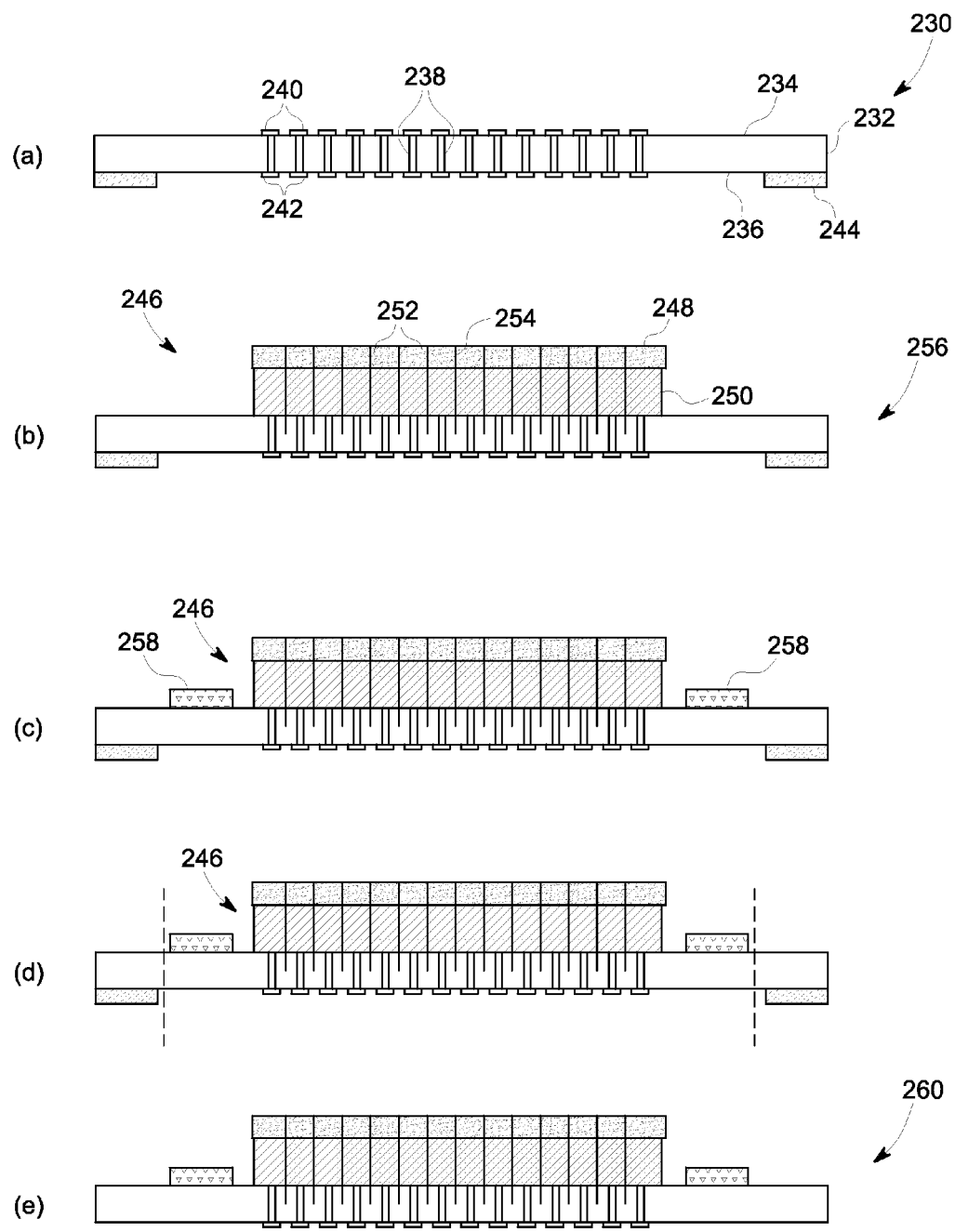
FIG. 14 is a diagrammatic illustration of a method of forming a sensor module of FIG. 2, in accordance with aspects of the present technique.

Furthermore, as depicted in FIG. 2, a sensor array may be indirectly coupled to an interconnect layer via use of an interposer. FIG. 14 depicts a diagrammatic illustration 230 of a method of forming the sensor module 60 of FIG. 2. The method includes providing an interposer 232, such as the interposer 64 of FIG. 2, as indicated by FIG. 14(*a*). The interposer 232 has a first side 234 and a second side 236. In a presently contemplated configuration, the interposer 232 includes an organic interposer. It may be noted that the interposer may also be formed using other materials having similar properties. Moreover, in accordance with aspects of the present technique, the interposer 232 includes one or more through vias 238, where the one or more through vias 238 are filled with an epoxy configured to optimize the performance of a sensor array. Additionally, a first set of contact pads 240 is disposed on the through vias 238 along the first side 234 of the interposer 232, while a second set of contact pads 242 is disposed on the through vias 238 along the second side 236 of the interposer 232. The first set of contact pads 240 aids in coupling a sensor array to the first side 234 of the interposer 232, while the second set of contact pads 242 aids in coupling the second side 236 of the interposer 232 to other electronics, such as an ASIC.

In addition, a first stiffener 244 is disposed on the second side 236 of the interposer 232. Also, in one embodiment, the first stiffener 244 may be glued to a portion of the second side 236 of the interposer 232. By way of example, the first stiffener 244 may be attached along the perimeter of the second side 236 of the interposer 232, in one embodiment. The first stiffener 244 is configured to support the interposer 232 to maintain rigidity and flatness of the interposer 232. The first stiffener 244 may be formed using stainless steel or by a ceramic member. It may be noted that stainless steel is used to form the first stiffener 244 because stainless steel has a CTE value of 11 ppm/° C., which closely matches the CTE value of the substrate. Furthermore, the first stiffener 244 may have a ring shape, a box shape, a circular shape, a rectangular shape, and the like.

Subsequently, as depicted in FIG. 14(*b*), a sensor layer 246 is provided. Particularly, the sensor layer 246 is disposed on the first side 234 of the interposer 232 to form a sensor array interposer stack 256. This sensor layer 246 may include a sensor array 248 and a support layer 250. Also, the sensor array 248 may have a thickness in a range from about 50 μm to about 3000 μm. In certain embodiments, the support layer 250 is configured to provide support to the sensor array 248. Further, if the sensor array 248 includes an ultrasound transducer array, the support layer 250 may also be configured to act as an ultrasound reflector. By way of example, for an ultrasound probe the support layer 250 is formed by tungsten carbide (WC) and serves to promote the outward direction of ultrasound energy.

Furthermore, as further depicted by FIG. 14(*b*), the sensor array 248 may be diced to form a plurality of sensor elements 252 prior to attaching the sensor array interposer stack 256 to other electronics. Reference numeral 254 is generally representative of the saw cuts. Dicing the sensor array 248 to form the sensor elements 252 after forming the sensor array interposer stack 256 but prior to coupling the sensor array interposer stack 256 to other electronics advantageously circumvents exposure of sensitive electronics such as ASICs to the severe vibrations and dust generated during the dicing process. Also, the use of the interposer 232 allows segregation of the sensor array forming process from the cleaner microelectronics attach process used to attach the sensor array interposer stack 256 to the ASIC.

It may be noted that if the sensor array 248 includes an ultrasound transducer array, the ultrasound transducer array 248 may include cMUTs, in one example. In such a case, the dicing step of FIG. 14(*b*) to form the plurality of sensor elements may be omitted.

Moreover, as depicted by FIG. 14(*c*), a second stiffener 258 is disposed on the first side 234 of the interposer 232. The second stiffener 258 is formed using steel or ceramic members. Particularly, the second stiffener 258 is formed using a material having a relatively high modulus. Furthermore, the second stiffener 258 is configured to support the interposer layer 232 that is typically formed using a material having a relatively low modulus. In addition, the second stiffener 258 is configured to provide a structurally stiff support for the interposer 232 on the first side 234, thereby providing a flat, unobstructed surface that allows for screen printing and other processing. In one embodiment, a low temperature process is used to attach the second stiffener 258 to the first side 234 of the interposer 232. Also, the first stiffener 244 is sawed off, as depicted by FIG. 14(d) resulting in a configuration of the sensor stack that allows stencil printing a fine pitch low temperature epoxy deposit to the contacts 242. In this case, the first stiffener 244 is used to support the structure during the fabrication of the sensor layer 246. However, the first stiffener 244 is subsequently removed to allow other operations to be performed on the contact pads 242. Further, as indicated by FIG. 14(e), a sensor stack 260 in formed. This sensor stack 260 may then be attached to a first side of an interconnect layer that may include one or more ASICs.

Figure 15:
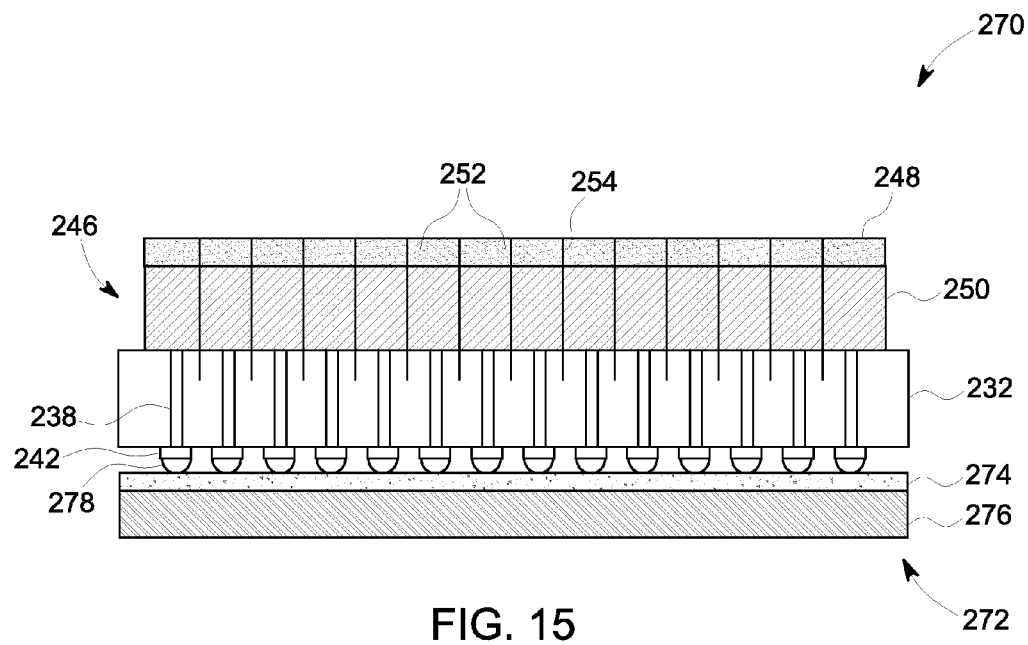
FIG. 15 is a diagrammatic illustration of one embodiment of a sensor module formed using the method of FIG. 14, in accordance with aspects of the present technique.

FIG. 15 depicts one embodiment 270 of a sensor module, such as the sensor module 60 of FIG. 2. In FIG. 15, the sensor stack 246 (see FIG. 14) is operationally coupled to an interconnect layer 272. As previously noted, the interconnect layer 272 may include a redistribution layer 274 and an integrated circuit 276, such as an ASIC. Particularly, in order to couple the sensor stack 246 to the interconnect layer 272, a plurality of stud bumps 278 may be disposed on the second set of metal pads 242 (see FIG. 14), in one embodiment. In certain embodiments, the stud bumps 278 may include gold (Au) stud bumps. An epoxy attach process is employed to attach the gold stud bumps to the second set of metal pads 242. These gold stud bumps 278 aid in maintaining a uniform height between the sensor stack 246 and the interconnect layer 272. The sensor stack 272 may be attached to the interconnect layer 272 using a low temperature process to form the sensor module 270.

It may be noted that since both the process of attaching the second stiffener 258 to the first side 234 of the interposer 232 and the process of attaching the sensor array interposer stack 256 to the interconnect layer 232 are carried out at relatively low temperatures (for example, temperatures below 100° C.), the sensor module 270 is not damaged. For example, low temperature for an ultrasound transducer material means that the material does not need to be repoled to ensure its piezoelectric property. Also, for a radiation detector, the material maintains high resistivity and good charge collection efficiency. Furthermore, some sensor modules are temperature sensitive. In particular, piezoelectric materials such as the commonly used lead zirconate titanate (PZT) lose their piezoelectric characteristics as the temperature approaches a characteristic temperature, $T_c$, the Curie temperature. For one common formulation PZT-5H, the Curie temperature is 190° C. Being able to process the interconnect at $T \ll T_c$ is advantageous since it avoids additional process steps that would be required to regenerate piezoelectric activity in the material. As will be appreciated, this process is called re-poling.

Figure 16:
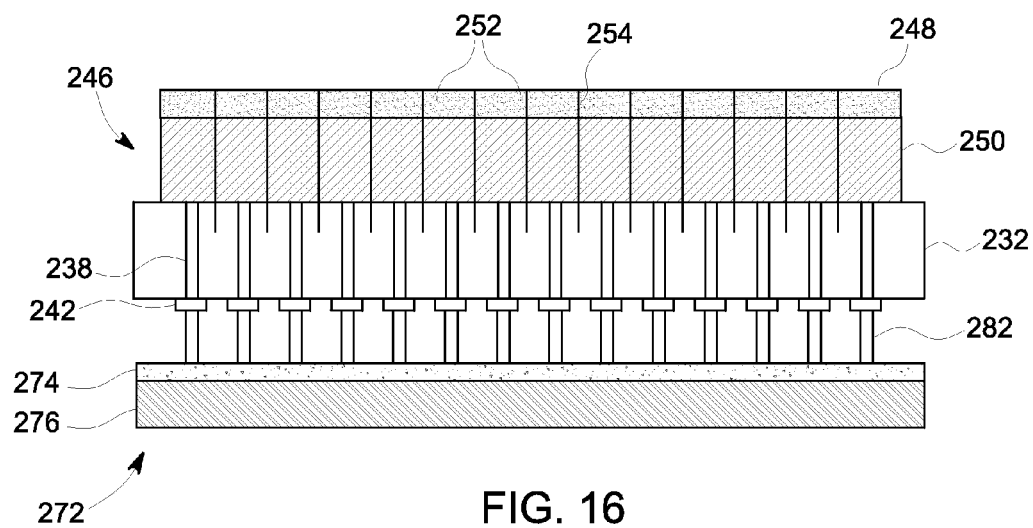
FIG. 16 is a diagrammatic illustration of another embodiment of a sensor module formed using the method of FIG. 14, in accordance with aspects of the present technique.

In accordance with further aspects of the present technique, the sensor stack 246 may be operationally coupled to the interconnect layer 272 using copper pillars instead of or in combination with the gold stud bumps 278 of FIG. 15. FIG. 16 depicts another embodiment 280 of a sensor module, such as the sensor module 60 of FIG. 2. Particularly, in FIG. 16, the sensor stack 246 (see FIG. 14) is operationally coupled to an interconnect layer, such as the interconnect layer 272 (see FIG. 15) via use of copper pillars 282. Accordingly, copper pillars 282 are disposed on the second set of metal pads 242 to aid in coupling the sensor stack 246 to the interconnect layer 272.

Figure 17:
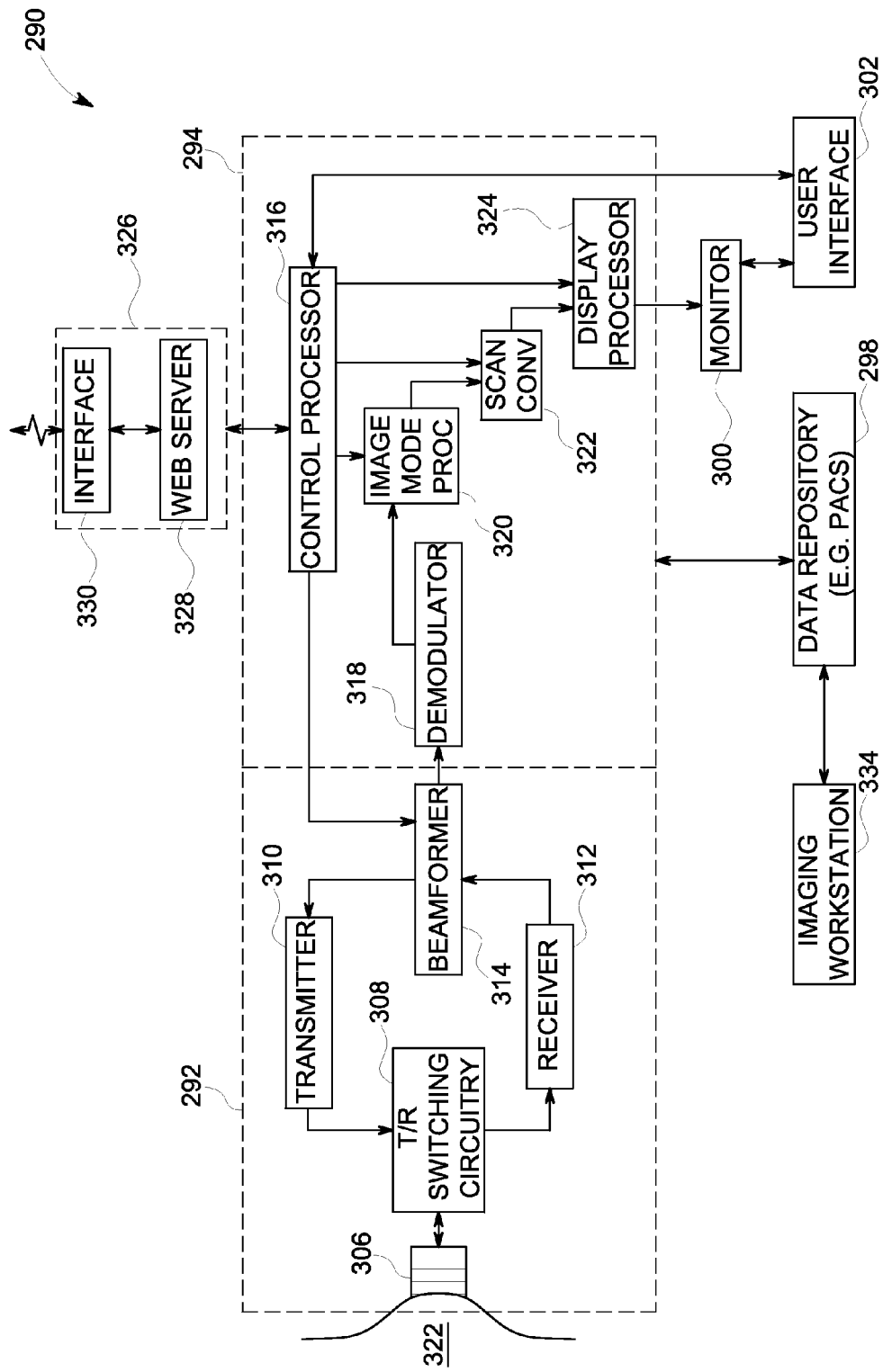
FIG. 17 is a block diagram illustration of an exemplary imaging system in the form of an ultrasound imaging system configured to use the exemplary detector modules of FIGS. 1-16.

According to further aspects of the present technique, the various embodiments of the detector modules described hereinabove may be employed in a medical imaging system, such as an ultrasound imaging system. FIG. 17 is a block diagram of an embodiment of an ultrasound imaging system 290. Furthermore, the ultrasound imaging system 290 is shown as including the acquisition subsystem 292 and the processing subsystem 294. The acquisition subsystem 292 may include a transducer assembly 306. In addition, the acquisition subsystem 292 includes transmit/receive (T/R) switching circuitry 308, a transmitter 310, a receiver 312, and a beamformer 314.

In one embodiment, the transducer assembly 306 may be disposed in an image acquisition device, such as an ultrasound probe. Also, in certain embodiments, the transducer assembly 306 typically includes a plurality of transducer elements (not shown) arranged in a spaced relationship to form a transducer array, such as a one-dimensional or two-dimensional transducer array, for example. In a presently contemplated configuration, the detector modules 150, 160, 170 and 180 may be used in the transducer assembly 306. Additionally, the transducer assembly 306 may include an interconnect structure (not shown) configured to facilitate operatively coupling the transducer array to an external device (not shown), such as, but not limited to, a cable assembly or associated electronics. The interconnect structure may be configured to couple the transducer array to the T/R switching circuitry 308.

The processing subsystem 294 includes a control processor 316, a demodulator 318, an imaging mode processor 320, a scan converter 322 and a display processor 324. The display processor 324 is further coupled to a display monitor 300 for displaying images. User interface 302 interacts with the control processor 316 and the display 300. The control processor 316 may also be coupled to a remote connectivity subsystem 326 including a web server 328 and a remote connectivity interface 330. The processing subsystem 294 may be further coupled to a data repository 298 configured to receive ultrasound image data. The data repository 298 interacts with an imaging workstation 334.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the present technique. Thus, those skilled in the art will appreciate that the ultrasound imaging system 290 is provided by way of example, and the present techniques are in no way limited by the specific system configuration.

In the acquisition subsystem 292, the transducer assembly 306 is in contact with a patient 332. The transducer assembly 306 is coupled to the transmit/receive (T/R) switching circuitry 308. Also, the T/R switching circuitry 308 is in operative association with an output of the transmitter 310 and an input of the receiver 312. The output of the receiver 312 is an input to the beamformer 314. In addition, the beamformer 314 is further coupled to an input of the transmitter 310 and to an input of the demodulator 318. The beamformer 314 is also operatively coupled to the control processor 316 as shown in FIG. 17.

In the processing subsystem 294, the output of demodulator 318 is in operative association with an input of the imaging mode processor 320. Additionally, the control processor 316 interfaces with the imaging mode processor 320, the scan converter 322 and the display processor 324. An output of the imaging mode processor 320 is coupled to an input of the scan converter 322. Also, an output of the scan converter 322 is operatively coupled to an input of the display processor 324. The output of the display processor 324 is coupled to the display 300.

The ultrasound system 290 transmits ultrasound energy into the patient 332 and receives and processes backscattered ultrasound signals from the patient 332 to create and display an image. To generate a transmitted beam of ultrasound energy, the control processor 316 sends command data to the beamformer 314 to generate transmit parameters to create a beam of a desired shape originating from a certain point at the surface of the transducer assembly 306 at a desired steering angle. The transmit parameters are sent from the beamformer 314 to the transmitter 310. The transmitter 310 uses the transmit parameters to properly encode transmit signals to be sent to the transducer assembly 306 through the T/R switching circuitry 308. The transmit signals are set at certain levels and phases with respect to each other and are provided to individual transducer elements of the transducer assembly 306. The transmit signals excite the transducer elements to emit ultrasound waves with the same phase and level relationships. As a result, a transmitted beam of ultrasound energy is formed in the patient 332 along a scan line when the transducer assembly 306 is acoustically coupled to the patient 332 by using, for example, ultrasound gel. The process is known as electronic scanning.

In one embodiment, the transducer assembly 306 may be a two-way transducer. When ultrasound waves are transmitted into the patient 332, the ultrasound waves are backscattered off the tissue and blood samples within the patient 332. The transducer assembly 306 receives the backscattered waves at different times, depending on the distance into the tissue they return from and the angle with respect to the surface of the transducer assembly 306 at which they return. The transducer elements convert the ultrasound energy from the backscattered waves into electrical signals.

The electrical signals are then routed through the T/R switching circuitry 308 to the receiver 312. The receiver 312 amplifies and digitizes the received signals and provides other functions such as gain compensation. The digitized received signals corresponding to the backscattered waves received by each transducer element at different times depend on the acoustic path lengths through the tissue. Also, the digitized received signals preserve the amplitude and phase information of the backscattered waves.

The digitized signals are sent to the beamformer 314. The control processor 316 sends command data to beamformer 314. The beamformer 314 uses the command data to form a receive beam originating from a point on the surface of the transducer assembly 306 at a steering angle typically corresponding to the point and steering angle of the previous ultrasound beam transmitted along a scan line. The beamformer 314 operates on the appropriate received signals by performing time delaying and focusing, according to the instructions of the command data from the control processor 316, to create received beam signals corresponding to sample volumes along a scan line within the patient 332. The phase, amplitude, and timing information of the received signals from the various transducer elements are used to create the received beam signals.

The received beam signals are sent to the processing subsystem 294. The demodulator 318 demodulates the received beam signals to create pairs of I and Q demodulated data values corresponding to sample volumes along the scan line. Demodulation is accomplished by comparing the phase and amplitude of the received beam signals to a reference frequency. The I and Q demodulated data values preserve the phase and amplitude information of the received signals.

The demodulated data is transferred to the imaging mode processor 320. The imaging mode processor 320 uses parameter estimation techniques to generate imaging parameter values from the demodulated data in scan sequence format. The imaging parameters may include parameters corresponding to various possible imaging modes such as B-mode, color velocity mode, spectral Doppler mode, and tissue velocity imaging mode, for example. The imaging parameter values are passed to the scan converter 322. The scan converter 322 processes the parameter data by performing a translation from scan sequence format to display format. The translation includes performing interpolation operations on the parameter data to create display pixel data in the display format.

The scan converted pixel data is sent to the display processor 324 to perform any final spatial or temporal filtering of the scan converted pixel data, to apply grayscale or color to the scan converted pixel data, and to convert the digital pixel data to analog data for display on the display 300. The user interface 302 is coupled to the control processor 316 to allow a user to interface with the ultrasound imaging system 290 based on the data displayed on the display 300.

Furthermore, the foregoing examples, demonstrations, and process steps such as those that may be performed by the imaging system 290, the acquisition subsystem 292 and/or the processing subsystem 294 may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository 298 or memory.

The methods for forming the detector modules and the various embodiments of the detector modules described hereinabove dramatically enhance the ability to form two-dimensional high-density tileable sensor arrays. Particularly, use of through silicon vias (TSVs) in the ASIC allow the routing of the power signals, ground signals, analog signals, and/or digital signals directly underneath the die. Additionally, the methods described hereinabove allow the sensor array to be attached to the top of the ASIC using a high temperature attach process to form a sensor stack. Also, the stacking of the sensor directly on top of the ASIC having the TSVs disposed therethrough allows the formation of a tileable element that can be handled similar to a flip chip die.

Moreover, multiple sensor stacks can be flip chip solder attached to a substrate to produce a very high-density detector module, with very tight chip-to-chip spacing. Also, these detector modules can be fashioned as pluggable detector modules. These pluggable detector modules can then be used to create a larger tileable array. This packaging concept offers the ability to create high-density detector arrays, such that when the entire stack is attached, the interconnect does not reflow. Also, a FRU detector module that can be formed by either plugging or soldering the detector modules to a substrate. Additionally, the method aids in creating a sensor stack on the interposer, and the coupling this stack on the ASIC. Additionally, this packaging concept can be used to create a very low profile and small package for use in portable systems.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for forming a tileable detector array, comprising:
    forming a detector module, comprising:
        providing a sensor array having a first side and a second side, wherein the sensor array comprises a first plurality of contact pads disposed on the second side of the sensor array;
        disposing the sensor array on an interconnect layer, wherein the interconnect layer comprises:
            a redistribution layer having a first side and a second side, wherein the redistribution layer comprises a second plurality of contact pads disposed on the first side of the redistribution layer;
            an integrated circuit having a plurality of through vias disposed therethrough, wherein a first side of the integrated circuit is operationally coupled to the second side of the redistribution layer, wherein the integrated circuit comprises a plurality of through vias disposed in a patterned arrangement on the first side and the second side of the integrated circuit and wherein the patterned arrangement of the through vias on the first side the integrated circuit is different from the patterned arrangement of through vias on the second side of the integrated circuit,
            wherein the sensor array is disposed on the interconnect layer such that the first plurality of contact pads on the second side of the sensor array is aligned with the second plurality of contact pads on the first side of the redistribution layer;
        operationally coupling the first plurality of contact pads on the second side of the sensor array to the second plurality of contact pads on the first side of the redistribution layer to form a sensor stack;
        coupling the sensor stack to a first substrate to form the detector module; and
    tiling a plurality of detector modules on a second substrate to form the tileable detector array.

2. The method of claim 1, wherein the sensor array comprises an ultrasound transducer array, a computed tomography detector array, an X-ray detector array, a positron emission tomography detector array, a photo-acoustic tomography detector array, or combinations thereof.

3. The method of claim 1, wherein the redistribution layer is configured to match an interface of the sensor array to an interface of the interconnect layer.

4. The method of claim 1, wherein operationally coupling the first plurality of contact pads on the second side of the sensor array to the second plurality of contact pads on the first side of the redistribution layer comprises employing a high temperature flip chip attach process to form the sensor stack.

5. The method of claim 1, wherein tiling the plurality of detector modules comprises using a flip chip attach process to attach the plurality of detector modules to the second substrate.

6. The method of claim 1, further comprising disposing a plurality of solder balls, a plurality of pins or a combination thereof on a second side of the second substrate to form a pluggable detector module.

7. The method of claim 6, further comprising disposing a plurality of pluggable detector modules on a third substrate to form a field replaceable unit.

8. The method of claim 7, further comprising operationally coupling the plurality of pluggable detector modules to the third substrate using solder bumps, stud bumps, posts, or combinations thereof.

9. The method of claim 1, further comprising coupling processing circuitry to a second side of the second substrate, wherein the processing circuitry comprises control electronics, front-end electronics, or both control electronics and front-end electronics.

10. The method of claim 9, wherein the coupling the processing circuitry to the second side of the second substrate comprises using solder bumps, stud bumps, posts, or combinations thereof.

11. A tileable detector array, comprising:
    a first substrate having a first side and a second side;
    a plurality of detector modules arranged on the first side of the first substrate, wherein each of the plurality of detector modules comprises:
        a sensor array having a first side and a second side, wherein a first plurality of contact pads is disposed on the second side of the sensor array;
        an interconnect layer comprising:
            a redistribution layer having a first side and a second side, wherein the redistribution layer comprises a second plurality of contact pads disposed on the first side of the redistribution layer;
            an integrated circuit having a plurality of through vias disposed therethrough, wherein a first side of the integrated circuit is operationally coupled to the second side of the redistribution layer, wherein the integrated circuit comprises a plurality of through vias disposed in a patterned arrangement on the first side and the second side of the integrated circuit and wherein the patterned arrangement of the through vias on the first side the integrated circuit is different from the patterned arrangement of through vias on the second side of the integrated circuit,
            wherein the sensor array is disposed on the interconnect layer such that the first plurality of contact pads on the second side of the sensor array is aligned with the second plurality of contact pads on the first side of the redistribution layer, and wherein the first plurality of contact pads on the second side of the sensor array is operationally coupled to the second plurality of contact pads on the redistribution layer; and
        coupling means disposed on a second side of the integrated circuit,
    wherein the plurality of detector modules is coupled to the first side of the first substrate via the coupling means disposed on the second side of the integrated circuit.

12. The tileable detector array of claim 11, further comprising a plurality of pins, a plurality of solder balls, or a combination thereof disposed on the second side of the substrate to form a pluggable detector module.

13. The tileable detector array of claim 12, further comprising a second substrate operatively coupled to one or more pluggable detector modules to form a field replaceable unit.

14. The tileable detector array of claim 13, wherein the second substrate comprises signal routing for supplying power and ground and signal transmission to and from the one or more pluggable detector modules.

15. The tileable detector array of claim 11, wherein the patterned arrangement of through vias on the integrated circuit comprises a two-sided pattern of through vias, a partial array of through vias, a full array of through vias, a pattern of through vias disposed along the perimeter of the integrated circuit, or combinations thereof.

16. The tileable detector array of claim 11, further comprising an interposer disposed between the sensor array and the interconnect layer.

17. The tileable detector array of claim 11, wherein the first substrate comprises a ceramic substrate or an organic substrate.

18. The tileable detector array of claim 11, further comprising processing circuitry coupled to the second side of the first substrate.

19. The tileable detector array of claim 18, wherein the processing circuitry is coupled to the second side of the first substrate using solder bumps, stud bumps, posts, or combinations thereof.

* * * * *